US010765437B1

(12) United States Patent
Antonio

(10) Patent No.: US 10,765,437 B1
(45) Date of Patent: Sep. 8, 2020

(54) CLIMBING HARNESS WITH BUILT-IN TOURNIQUET

(71) Applicant: Ishmael L. Antonio, Rio Rancho, NM (US)

(72) Inventor: Ishmael L. Antonio, Rio Rancho, NM (US)

( * ) Notice: Subject to any disclaimer, the term of this patent is extended or adjusted under 35 U.S.C. 154(b) by 612 days.

(21) Appl. No.: 15/255,427

(22) Filed: Sep. 2, 2016

Related U.S. Application Data

(60) Provisional application No. 62/213,692, filed on Sep. 3, 2015.

(51) Int. Cl.
*A61B 17/132* (2006.01)
*A62B 35/00* (2006.01)

(52) U.S. Cl.
CPC ...... *A61B 17/1325* (2013.01); *A62B 35/0006* (2013.01)

(58) Field of Classification Search
CPC .... A45F 3/14; A45F 3/15; A45F 3/047; A45F 2003/045; A45F 2003/142; A45F 2003/144; A45F 2003/146; A45F 2003/148; A61B 17/00; A61B 17/132; A61B 17/1327; A61B 17/1322; A61B 17/1325; A61B 5/025; A61H 39/04; A62B 35/00; A62B 35/0006; F16B 45/02
See application file for complete search history.

(56) References Cited

U.S. PATENT DOCUMENTS

| | | |
|---|---|---|
| 5,067,585 A | 11/1991 | Bell |
| 5,413,262 A | 5/1995 | Dewire et al. |
| 5,464,136 A | 11/1995 | Eddy |
| 6,371,346 B1 | 4/2002 | Sharma |
| 6,481,528 B2 | 11/2002 | Antonio |
| 6,637,077 B2 | 10/2003 | Doty |
| 6,732,834 B2 | 5/2004 | Colorado |
| 6,899,720 B1 | 5/2005 | McMillan |
| 7,103,943 B2 | 9/2006 | Lambert |
| 8,348,970 B2 | 1/2013 | Janota |
| 8,499,421 B2 | 8/2013 | Espinosa |
| 8,573,359 B2 | 11/2013 | West |
| 8,887,866 B2 | 11/2014 | Petty et al. |
| 2011/0067953 A1 | 3/2011 | Kopp |
| 2014/0090140 A1* | 4/2014 | Craig ........... A41D 1/06 2/2.5 |

FOREIGN PATENT DOCUMENTS

| | | | |
|---|---|---|---|
| EP | 1712259 A2 | 10/2006 | |
| WO | WO2015100260 | * 7/2015 | ........... A63B 55/00 |
| WO | WO2015119968 | * 8/2015 | ........... A61B 17/132 |

OTHER PUBLICATIONS

"Pocket Tourniquets," Web Log Post at htttp://pig-monkey.com; Feb. 1, 2015.

* cited by examiner

*Primary Examiner* — Wade Miles
*Assistant Examiner* — Mikail A Mannan
(74) *Attorney, Agent, or Firm* — Rod D. Baker

(57) ABSTRACT

A system of a combined climbing harness and medical tourniquet, and a method for using the system. A looped thigh strap portion of a climbing harness is detachable from the harness belt for separate alternative use as an emergency tourniquet for the user or a patient. The looped thigh strap is provided with features and components to facilitate its use as a functional tourniquet for either an arm or a leg, while nevertheless in ordinary use allowing it to serve as a component of a climbing harness.

19 Claims, 13 Drawing Sheets

US 10,765,437 B1

CLIMBING HARNESS WITH BUILT-IN TOURNIQUET

CROSS REFERENCE TO RELATED APPLICATIONS

This application claims the benefit of U.S. Provisional Patent Application Ser. No. 62/213,692 entitled "Climbing Harness with Built-In Tourniquet" filed on 3 Sep. 2015, the entire disclosure of which is hereby incorporated by reference.

BACKGROUND OF THE INVENTION

Field of the Invention

This invention relates to climbing harnesses and belts, and specifically to such a type of harness system incorporating an emergency medical tourniquet.

Background

To conduct high angle (steep climb and down rappel) climbing operations, such as in mountaineering and rock climbing, but also including in tactical assaults or rescues in buildings, users (climbers, rescue technicians, tactical operators, law enforcement, etc.) wear a climbing harness system with leg loops. Climbing harness systems have been devised for use by recreational climbers, as well as for use by military and law enforcement personnel. Similar requirements arise in the event of urban assaults, searches, and rescues on cliffs or steep mountainous terrain. In order to perform high angle maneuvers using climbing ropes, a user must be equipped with some sort of climbing harness by which the user removably and controllably engages with the climbing rope or ropes deployed in the operation. A known type of harness system is disclosed in U.S. Pat. No. 6,481,528 to Antonio, the teachings of which are incorporated herein by reference.

Under many circumstances when a climbing harness is in use, there is potential for encountering personal injury, to the user or a colleague climber, or to another person being rescued. Indeed, in some rescue situations, the user's overriding goal is to reach an injured person to provide first aid. Personal injuries may include severe bleeding, including arterial or venous bleed, which may require the use of a medical tourniquet. An individual user may, himself, suffer a severe bleeding as a result of an accident during the climbing operations. Accordingly, it is highly desirable for a user always to have at the ready an emergency tourniquet apparatus. Presently there is no integrated harness and tourniquet apparatus known to be available.

With the foregoing background, the presently disclosed invention was developed. Particularly, there is disclosed a method for using a modular tourniquet and harness system.

SUMMARY OF THE INVENTION

There is disclosed an apparatus and method for providing a medical tourniquet in operative combination with a climbing harness. A thigh loop or strap portion of a climbing harness system is detachable from the harness belt portion for separate alternative use as an emergency tourniquet for the user or a patient. The thigh strap portion is provided with features and components to facilitate its use as a functional tourniquet for either an arm or a leg, while nevertheless allowing it to serve as a component of a climbing harness in ordinary use.

BRIEF DESCRIPTION OF THE DRAWINGS

The attached drawings, which form part of this disclosure, are as follows.

Like elements are labeled with like numerals in the several views; the drawings are not necessarily to scale, within a view or relative to each other.

DETAILED DESCRIPTION OF THE INVENTION

Figure 1:
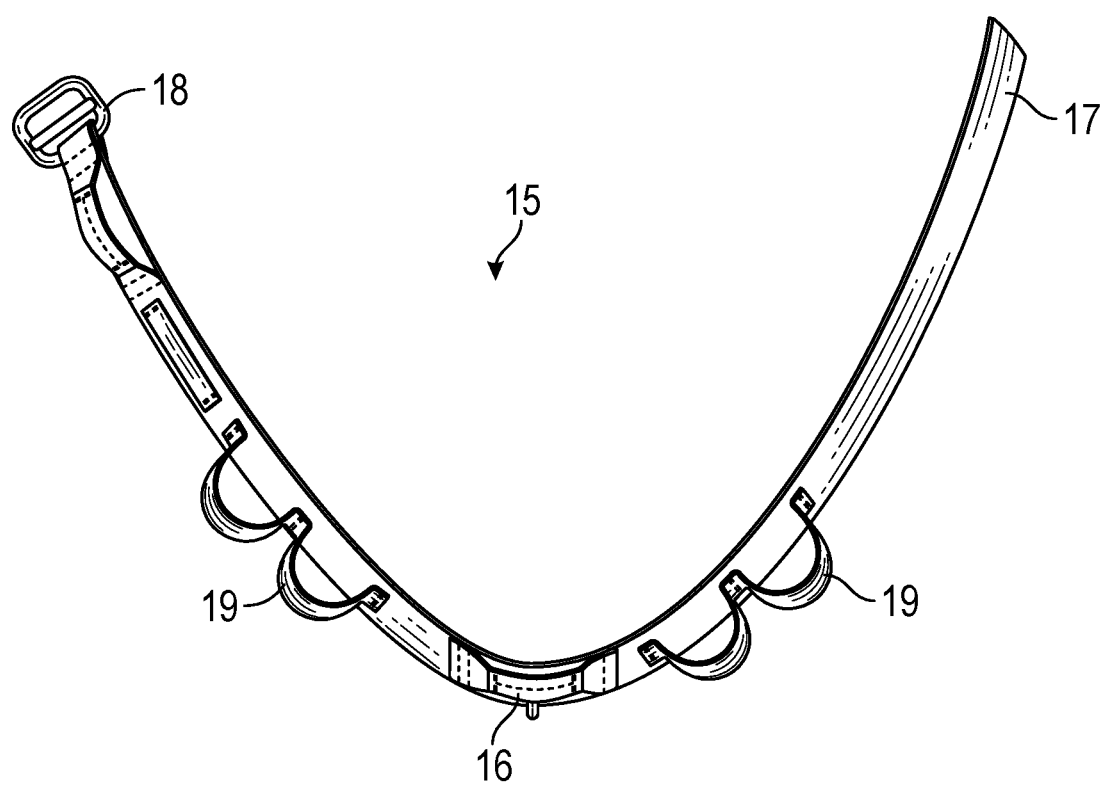
FIG. 1 is a perspective view of a climbing harness belt, as known generally in the art, and which forms a part of the complete apparatus according to the present disclosure.

This invention relates to climbing harnesses, such as those worn by rock climbers, or by law enforcement or military personnel, e.g., when rappelling down a cliff/wall or lowering via a rope from a hovering helicopter. Climbing/rappelling harnesses typically include some sort of waist belt integrated with a pair of thigh straps. Ideally, to simplify and speed use of, as well as assure the ready availability of, a suitable medical tourniquet, a modular system is provided herein for combining a tourniquet with a climbing harness, such that the tourniquet is always available when the harness system is in use. A tourniquet according to the present disclosure qualifies as a USA Food and Drug Administration (FDA) Class I medical device; properly constructed the disclosed combination harness/tourniquet is eligible for certification by the International Climbing and Mountaineering Federation (UIAA).

Emergency tourniquets are tight bands applied to injured limbs meant to stop the loss of blood in emergency situations. Tourniquets can save lives when it's difficult to receive medical attention in a timely manner. They are not a long-term solution for any severe injury, but can be effective at controlling bleeding in the short term until the wound can be treated by trained professionals and/or in an improved treatment venue. It is important to learn how to use a tourniquet, because improper technique (or leaving it on too long) can actually lead to dire complications, such as tissue death and amputation. Thus a tourniquet normally is only used on arm(s) or leg(s) where there is danger of loss of a patient's life. The tourniquet according to the present disclosure is a basic emergency tourniquet intended for use as first aid until advanced medical care is available. Advanced surgical (e.g., pneumatic) tourniquets known for use in a hospital setting are not implicated by this disclosure.

The disclosed system assures that a tourniquet is at hand for rapid deployment and use during climbing operations. According to the system and method, the tourniquet portion also is a component of the harness system. Accordingly, a climber using the present apparatus cannot forget to bring along a suitable tourniquet, or through complacency or hurry deliberately chose not to bring along a tourniquet, to a climbing scenario. If the climber is using a complete harness system according to this disclosure, he automatically has on his person a tourniquet for use on himself or another person in the event of a medical emergency.

By way of general introduction, the system according to the present invention includes a main belt portion and two thigh strap portions, which when in combined use constitute a climbing harness. When needed, at least one of the thigh straps doubles in function as a medical tourniquet according to the further descriptions herein below. Thus a main aspect of the disclosed invention is the incorporation of tourniquet features into a climbing harness thigh strap. For reference to the known art, a thigh strap somewhat similar to a strap seen in my U.S. Pat. No. 6,481,528, may be innovatively modified according to the present disclosure to include elements that enable a harness thigh strap to function alternatively as a tourniquet.

The harness thigh strap according to the present disclosure has thereon a main strap loop by which a lockable carabiner can be removably attached to an end of the thigh strap. There also is provided on the thigh strap a "carabiner holder loop" to which a torsion tool, preferably a climbing carabiner, can be engaged or attached and then twisted to initiate a tourniquet procedure. Proximate to the first carabiner holder loop is a second loop on the thigh strap. "Proximate" means less than about six inches; in a preferred embodiment, the proximity of the second loop to the first carabiner loop corresponds generally to the functional length of a standard climbing carabiner (e.g., about three to four inches). Thus when a carabiner is used as a torsion tool to tighten the carabiner loop, the windlass carabiner can be opened, clipped to the second loop, and then closed thereby to maintain the carabiner in its tightened position to hold the thigh strap in a tightened tourniquet condition about the injured limb.

In an emergency, the thigh strap can be used as a tourniquet to stanch heavy venous and/or arterial bleeding in a victim's limb (arm or leg). In such use, the thigh strap is partially or fully detached from the load-bearing main belt of the harness, and then looped around the injured limb. The carabiner on the tourniquet thigh strap is manually twisted to tighten the thigh strap (by effectively shortening its looped length). When sufficiently thus tightened in place above the wound, the windlass tourniquet carabiner (while still fastened through the carabiner holder loop of the tourniquet strap) is then temporarily but securely clipped through the second loop on the strap to hold the thigh-strap/tourniquet in its twisted/tightened condition. According to the invention, therefore, a user of the climbing harness has a tourniquet readily at hand as an associated portion (thigh strap) of the harness.

Figure 4:
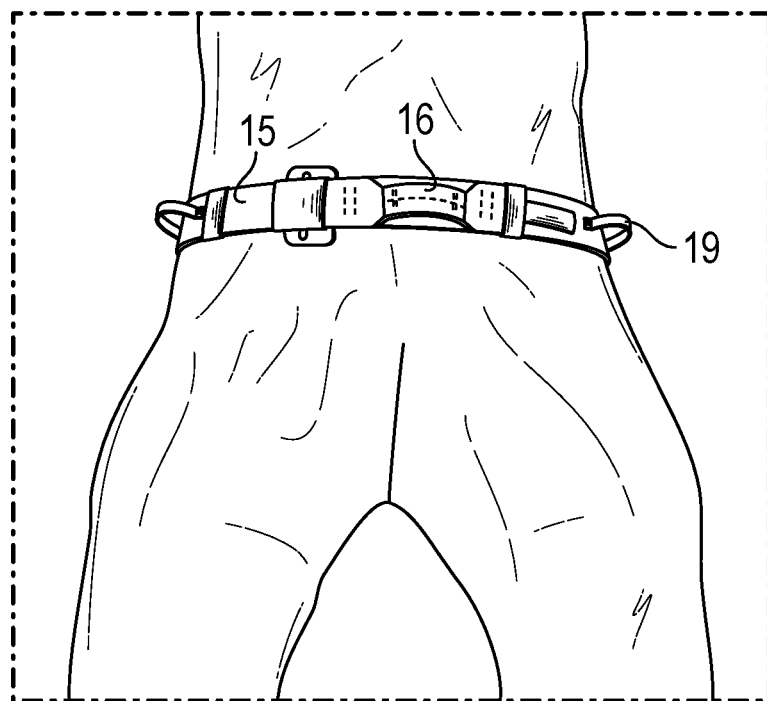
FIG. 4 is a front view of the climbing harness belt portion of the present system, shown positioned in place upon the hips of a user according to the present disclosure.

Attention is invited first to FIG. 1, illustrating a load-bearing climbing harness belt 15 which serves as the main belt portion of the tourniquet harness system according to this disclosure. The main belt 15 is generally according to the prior art, although it is very preferred according the present invention to provide on the belt a sturdy center loop 16. The load bearing belt 15 can be practically any type of climbing harness-type belt known, provided there is a climbing-rated center loop means 16 secured on the belt 15 through which a climbing-rated carabiner may be securely, yet removably, attached to the belt. The belt 15 and loop 16 are both rated according to applicable safety standards for use as weight-bearing climbing harness components. When in use according to this disclosure, the belt 15 is adjusted on the user's body so that the central loop 16 is situated generally to the center-front of the user's body (i.e., in the general vicinity of the navel, as seen in FIG. 4).

In use, the belt 15 is reliably fastened about the user's body by engaging the free end 17 of the belt with an appropriate buckle 18 (e.g., a ladder buckle or other adequately rated buckle type known in the art of climbing apparatus). The belt 15 should be suitable for use as a National Fire Protection Association Class 1 harness; combined with appropriate leg loops (thigh straps) the harness system should qualify as NFPA Class 2 sitting harness. Various auxiliary loops 19 may be provided on the belt 15 for attachment of gear or the like generally according to convention.

Figure 2:
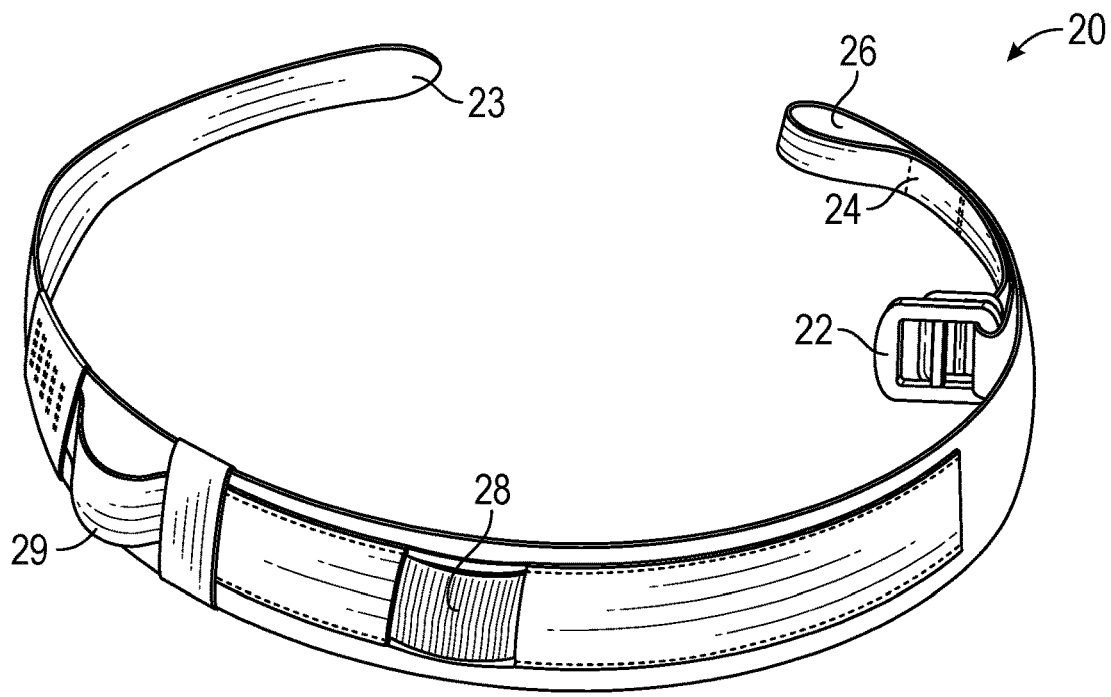
FIG. 2 is a perspective view of a tourniquet thigh strap portion of the apparatus of the present disclosure, shown in a released or open condition.
Figure 3:
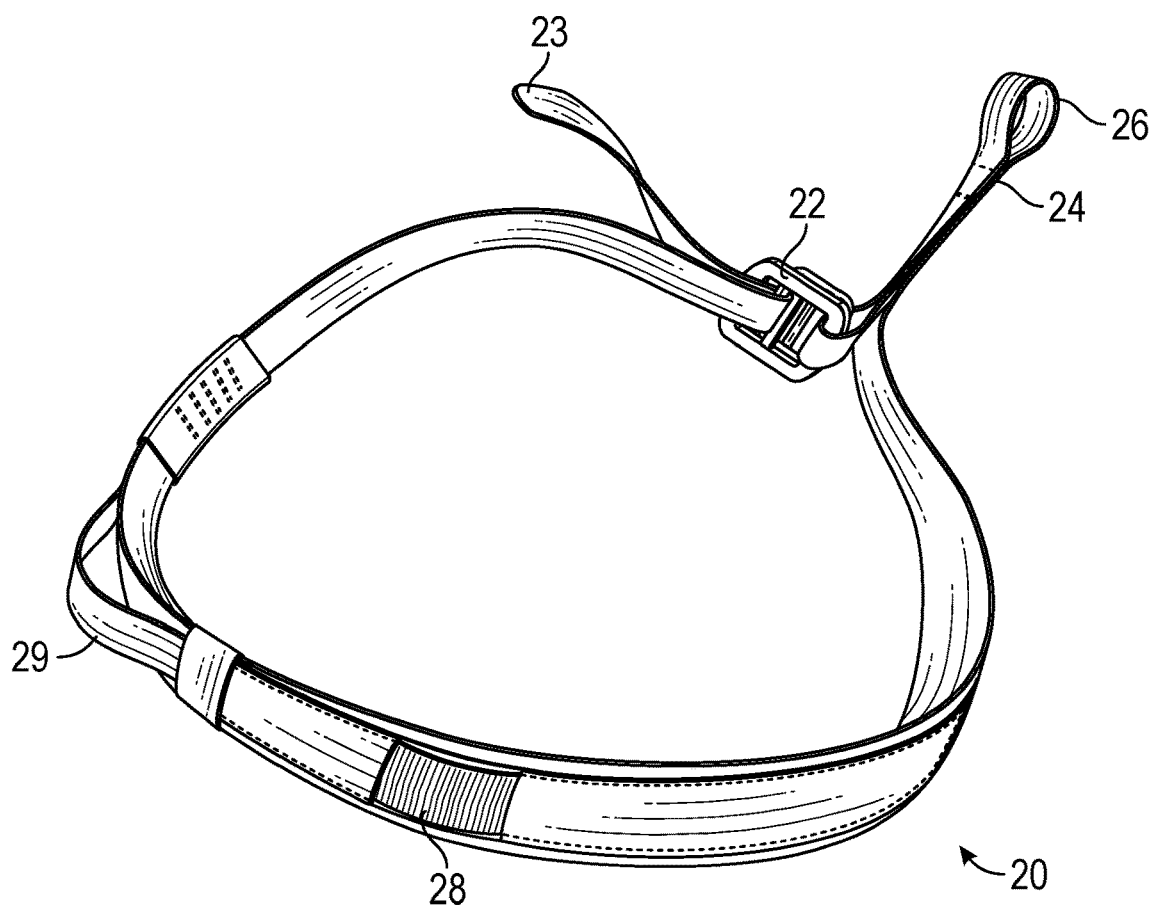
FIG. 3 is a perspective view of the tourniquet thigh strap portion of the apparatus shown in FIG. 2, shown in a closed loop condition.

FIGS. 2 and 3 show a thigh strap portion 20 of a harness according to the present disclosure. While this component is referred to as a "thigh strap" or "thigh strap portion" herein, it is to be understood throughout this disclosure that the strap 20 also alternatively serves as a tourniquet strap when deployed and used according to the present invention. A Class 2 harness employs two thigh straps. In a harness system and method according to the present disclosure, two thigh straps preferably are used; by this invention, at least one of the two thigh straps is a thigh strap 20 adapted for alternative use as a tourniquet according to this disclosure. (The other thigh strap may be more similar to leg loops of the known art, or may also be a tourniquet strap 20 according to this disclosure.) Thigh strap 20 is shown in an open position or condition in FIG. 2, and in a looped closed condition in FIG. 3. In use during climbing, the strap 20 is looped around the user's thigh, and closed by means of a buckle 22 (see FIG. 5). When used as a tourniquet, the strap 20 also is in the closed condition, as described further herein.

The thigh strap 20 is fabricated of nylon webbing, or the like, as known in the art of climbing equipment, and has a buckle 22 for releasably fastening the strap 20 around a user's thigh. The buckle 22 preferably is a self-locking type buckle in common use for harness thigh straps, and may be a COBRA™ quick-release buckle available from AustriAlpin, Inc. of Crowsnest Pass, Alberta, Canada. The first or free end 23 of the thigh strap 20 can be engaged securely yet releasably with/through the buckle 22 to secure the thigh strap in the closed condition (FIG. 3) during climbing. Depending upon the particular type of suitable buckle used, the first or free end 23 of the strap 20 alternatively may also have a second buckling component (not shown in the drawing figures, but known in the art) of a two-part buckling device, for secure engagement with the first buckle part 22.

It is observed in FIGS. 2 and 3 that the buckle 22 is not attached to the topological second or other end 24 of the strap 20. Rather, the strap 20 and buckle element 22 are configured such that the buckle 22 is attached to and available at an intermediate location on the strap, a modest distance from the topological second end 24. Instead, the second end 24 of the strap features and defines a secure main strap loop 26. The main strap loop 26 optionally may be defined by folding the webbing or strap body to double it back upon itself, and then be sewn securely to itself, as seen best in FIG. 3. The strap loop 26 thus is defined as a closed loop in the strap at the strap's second end, while the actual terminus of the body of the strap's webbing or other strip of material is used to permanently secure the buckle element 22 to a medial location on the strap 20—again as best indicated in FIGS. 2 and 3.

The strap 20 includes a torsion tool or carabiner holder loop 28. In a preferred embodiment, the holder loop 28 is a carabiner holder loop. The holder loop 28 may be fabricated from a short strip of elasticized fabric or flexible, yet durable, material securely fastened at an intermediate location on the length of the strap 20. The carabiner holder loop 28 permits a carabiner (not shown in FIGS. 2 and 3) or other torsion item to be inserted there under (between it and the body of the strap 20) and engaged or clipped in place upon the strap 20. If as preferred the torsion item is a carabiner, it is engaged with the holder loop in a manner of releasably attaching a carabiner to a loop ordinary in the art of climbing and rappelling. However, the holder loop 28 is composed of an adequate length of material, and is so configured and attached to the body of the strap 20, so as to withstand severe twisting of the loop 28 without the body of the loop 28 failing, or detaching from the main body of the strap 20. A "windlass" carabiner clipped in place upon the holder loop 28, or some other torsion tool (such as a dowel-like item) is inserted into the loop, and is rotated to twist the loop 28 when the strap 20 is in use as a tourniquet, as described further herein.

The thigh strap 20 is provided with at least one other loop, besides the holder loop 28, in substantially close proximity (e.g., about the length of a climbing carabiner) to the holder loop 28. This second loop 29 is used to retain in place a torsion item, such as a carabiner, after the carabiner has been used as a windlass and has been twistably rotated to tighten the holder loop 28 to perform the tourniquet operation. In a preferred embodiment of the apparatus, the strap 20 features a second loop 29 that is a sturdy autoblock or autobrake loop extremely well-secured onto or with the body of the strap. The second or autoblock loop 29 preferably is located nearby the carabiner holder loop 28 to be used as the second loop for maintaining in tightened condition the windlass carabiner during the tourniquet procedure.

The second loop 29 preferably is secured in the strap 20 so to be rated for use in connecting to the strap 20 a climbing autoblock device (e.g., an accessory cord tied in an autoblock hitch or friction knot). An autoblock device (not shown in the drawings) may also include a carabiner, and various such devices are known in the art to connect a harness thigh strap to a climbing/rappelling rope for the purpose of providing a safety "back up" in the event of a user's accidental fall. Thus the second loop 29 optionally, in an embodiment of the system, may fulfill dual functions as a means for engaging an autoblock device, and as a means for holding in tightened condition a windlass carabiner during a tourniquet application.

FIG. 4 depicts a harness belt 15 as worn by the user of the present system. In FIG. 4, the harness belt 15 is seen as it would be fitted upon the user at the outset of the practice of the present invention. The belt 15 is wrapped snugly around the user's upper hips, and releasably secured by means of the buckle 18. It is noted that the belt is positioned upon the user's body so that the heavy-duty, central, carabiner loop 16 is situated generally centrally at the front of the user's body. A climbing carabiner or other suitable belay device (not seen in FIG. 4) known in the art is releasably attached to the carabiner loop 16 in a manner known in the art for releasably connecting a harness belt to a rope in use for climbing rappelling.

Figure 5:
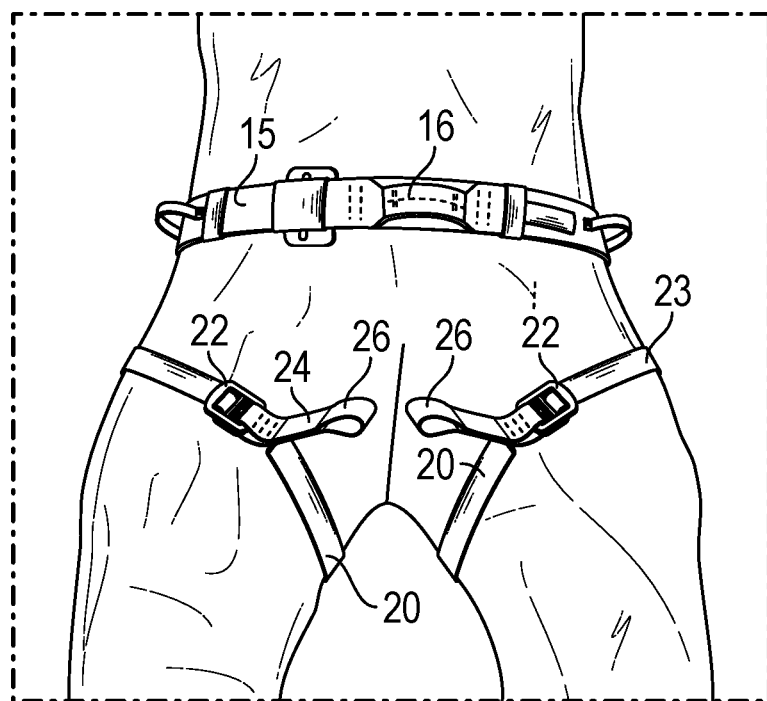
FIG. 5 is a front view of the climbing harness belt, and two harness thigh straps, according to the present disclosure and shown in position for use upon the hips and upper thighs of a user.

The further placement of the present system is depicted in FIG. 5, illustrating how two thigh straps are disposed upon a user for use. Again, either one, or both, the thigh straps may be according to the present disclosure, capable of fulfilling the alternative role of a medical tourniquet. In FIG. 5, each thigh strap 20 is wrapped around the user's upper thigh, in a conventional location. The first or free end 23 of each strap is releasably but securely engaged with its respective strap buckle 22 so that the strap 20 defines a securely closed loop. Each of the two strap loops 26 is situated to hang or extend from the front of the user's thigh. There is a length of thigh strap of sufficient hanging length such that both strap loops 26 can be brought up to the proximity of the carabiner loop 16 on the belt 15, while maintaining a proper positioning of the thigh straps upon the user's thighs.

Figure 6:
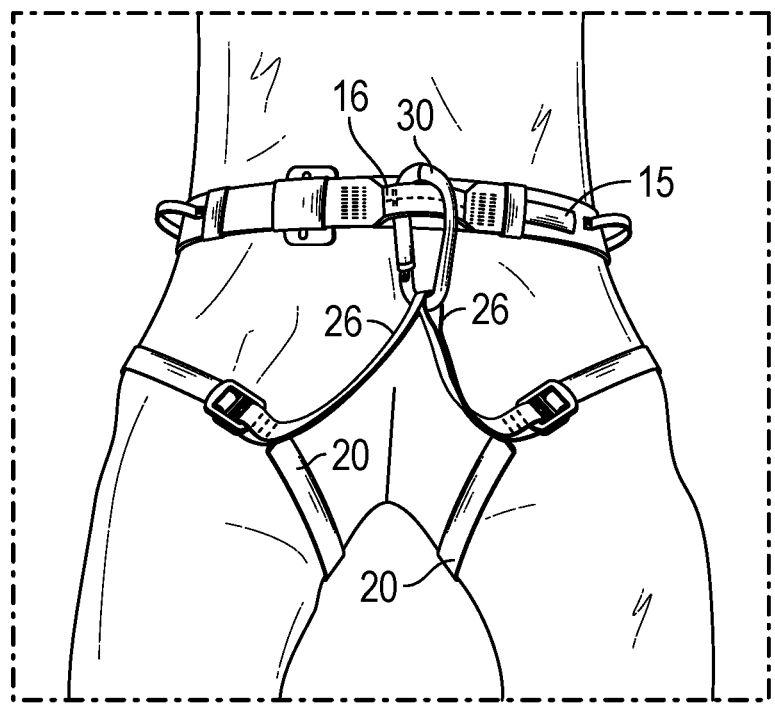
FIG. 6 is a front view similar to the view of FIG. 5, of the climbing harness belt and two harness thigh straps, with a carabiner shown in use to connect a loop on the harness belt with loops on the thigh straps, to provide for a sitting harness system.
Figure 7:
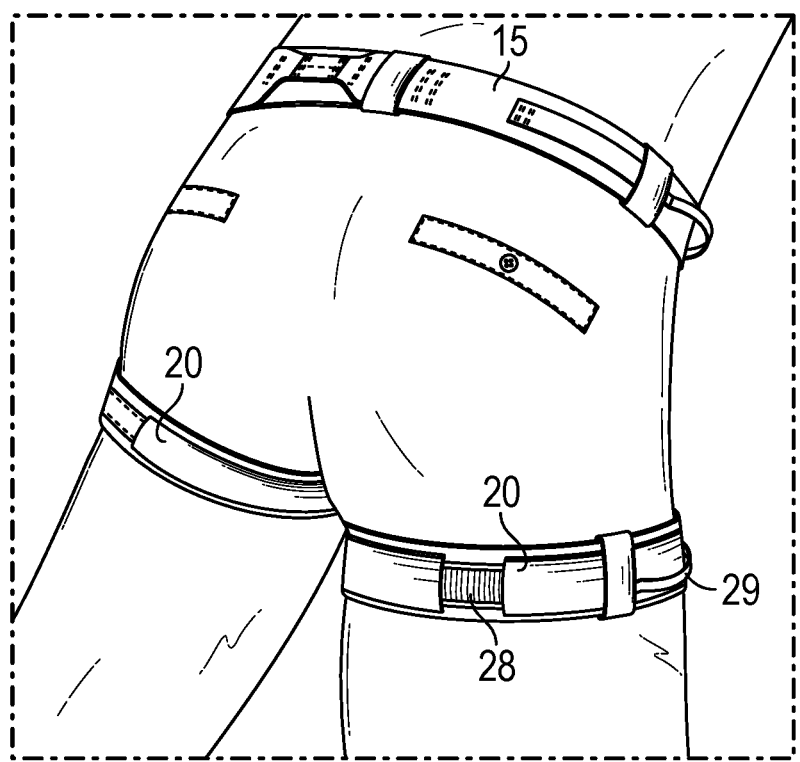
FIG. 7 is a rear view of the sitting harness system of FIG. 6, according to the present disclosure, in use upon a user's body.

FIG. 6 illustrates a next step of placing the harness system on the user. A rated main carabiner 30 (or other suitable known belay device known in the art) is used to bring and hold together the belt's carabiner center loop 16 and the two strap loops 26, as seen in FIG. 6. The main carabiner 30 is loopably disposed through all three loops 16, 26, and closed according to conventional practice. A climbing/rappelling rope (not shown) may then be engaged with/though the carabiner 30 for use in climbing/rappelling, as well-known. When properly installed upon the climber's body for use in climbing/rappelling, the belt 15 and both thigh straps 20 encircle the climber's waist/hips and upper thighs, to provide an appropriate sitting harness which is seen in the rear view of FIG. 7. FIG. 7 shows the carabiner holding loop 26, as well as the autoblock or second loop 29 upon the right thigh strap 20.

Figure 8:
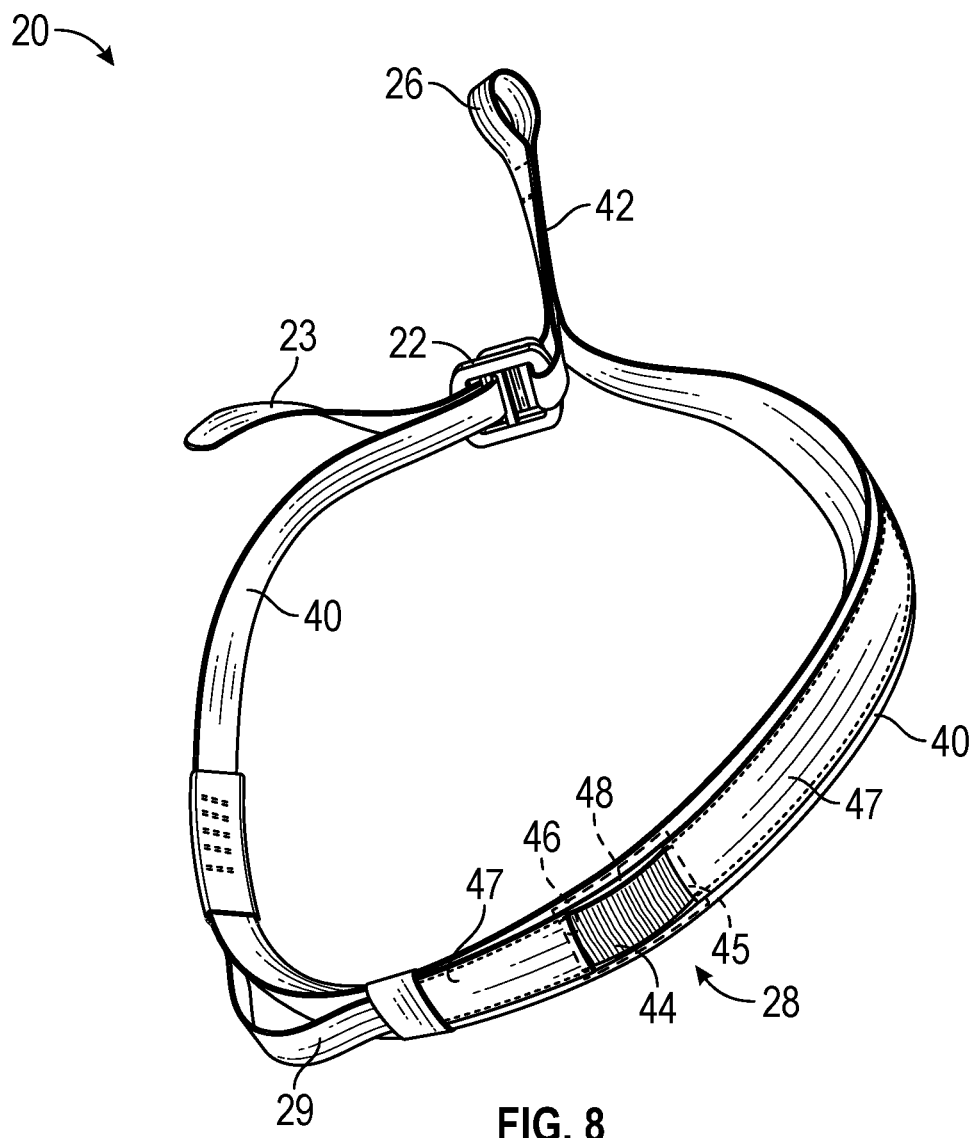
FIG. 8 is an enlarged view of a single thigh strap portion of the apparatus and system of the present disclosure, showing additional details of the thigh strap.

Reference is made to FIG. 8. When detached from the harness belt 15 (e.g., by being disconnected from the main carabiner 30), the thigh strap 20 has alternative utility as a tourniquet. It is here noted that in many versions of sitting harness known in the art, a thigh strap may not be readily detachable from its associated harness belt; indeed some thigh loops would have to be cut and severed for such detachment.

The thigh strap 20 has a main body 40 composed of a durable strip or tube of suitable material (typically, woven nylon webbing) known in the art for fabrication of climbing harness components. A segment 42 of the body 40 is doubled back and sewn securely to itself to define the climbing rated strap loop 26. To functional alternatively as a tourniquet, the thigh strap advantageously is provided with the holder loop 28. The holder loop 28 preferably is composed of a strip 44 of durably reinforced, substantially rip-proof, yet flexible and optionally very mildly elastic fabric. The loop strip 44 has its two ends 45, 46 sewn securely to the body 40 of the thigh strap. The carabiner holder loop strip 44 preferably has its respective ends 45, 46 secured, as by sewing, between the strap's main body 40 and a reinforcing overlay layer 47 which itself is affixed permanently to the body 40. The carabiner holder loop strip 44 defines the loop 28 which distends a modest distance out from the body 40. An item, such as a carabiner, can be disposed between the carabiner holder loop strip 44 and the body 40 and then rotated about an imaginary axis oblique to the body 40, in order to twist the carabiner holder loop strip 44 around the item. With the strap buckle 22 engaged to keep the thigh strap 20 in the closed condition, the twisting of the carabiner holder loop strip 44 with the carabiner or other item shortens the effective looped length of the thigh strap body to yield the desired tourniquet effect. In an alternative embodiment of the system, the strap body 40 is provided with a stiffener element 48 secured thereto or therein in the adjacent proximity of the carabiner holder loop strip 44. The stiffener element 48 may be, for example, strip of thin plastic layer that is mildly bendable (to permit the strap body 40 to conform to the contour of a user's thigh), and yet is stiff to ameliorate or prevent the body 40, near the carabiner holder loop strip 44, from twisting significantly during the twisting/wrapping of the carabiner holder loop strip 44 during tourniquet operations. The stiffener element 48 may be disposed within the interior of the strap body 40, when that body is composed of a tube of woven nylon.

FIGS. 9A-J collectively supply serial illustrations of selected steps of a method for practicing the invention of the present disclosure. A user may be using the harness system including the harness belt 15 and a pair of thigh straps 20 to execute roping maneuvers in climbing/rappelling in recreational, law enforcement, rescue or military circumstances. During such usage, the system of this disclosure is configured as shown generally in FIGS. 6 and 7. There may be one or more climbing ropes (not shown) disposed through and/or engaged with the main carabiner 30 according to known climbing techniques. Also, there may be an autobrake device/assembly and/or cord in connective disposition between a thigh strap's autobrake second loop 29 and a climbing rope in use. While or after maneuvering, the climber encounters an emergency in which one of her limbs, or the limb(s) of a victim or colleague, is bleeding profusely, indicating the expeditious need to apply a medical tourniquet.

Figure 9A:
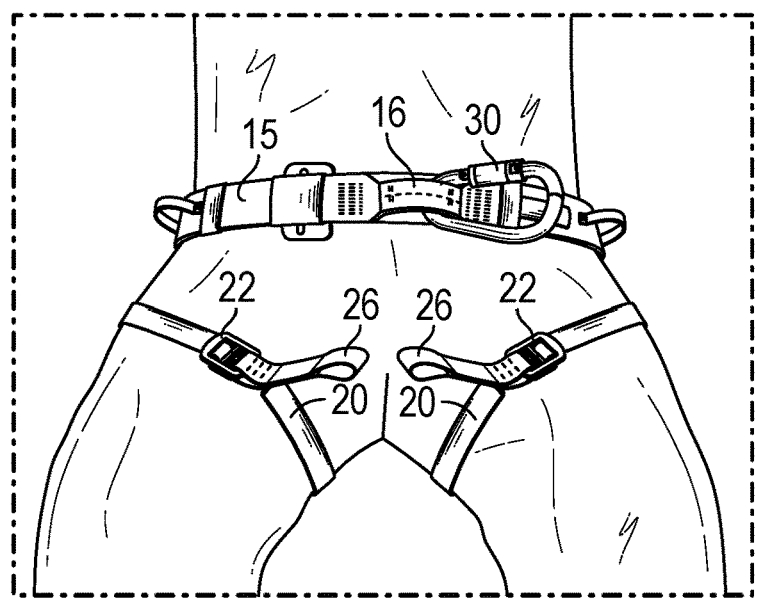
FIG. 9A is a front view of a combined tourniquet and climbing harness system according to the present disclosure, showing a step of disengaging the harness thigh straps from a main carabiner to release or detach the thigh straps from the harness belt.

In the emergency situation, the climber opens the main carabiner 30 (on the belt's main carabiner loop 16) and detaching it from the loops 16 and 26, in order to disengage from the main belt portion 15 one or both thigh straps, but at least the special thigh strap 20 to be used as a tourniquet. This step of disengaging from the main carabiner 30 the strap loops 26 of the thigh straps 20, and the resulting disposition of the harness system, are seen in FIG. 9A. A thigh strap 20 thus disengaged is configured generally as shown in FIGS. 3 and 8.

A disengaged thigh strap 20 is thereby detached from the harness belt 15, and thus is ready to be used as a tourniquet. If the strap 20 is to be used on a second person, in its looped condition (e.g., FIG. 3) it is applied to the patient's injured limb, between the bleeding injury and the patient's heart, generally in accordance with known tourniquet technique. If the climber is applying the tourniquet strap to himself, he rapidly places the looped thigh strap 20 around his own limb, also according to conventional principles of medical tourniquet use. For purposes of illustration, FIG. 9B shows the thigh strap 20 in initial use as a tourniquet applied to the climber's own upper right leg; it is immediately understood that instead of the exemplary instance of usage of the invention on the user's leg, the tourniquet thigh strap 20 may rapidly be applied (by the user or by a second person) to one of the user's three other limbs, or to any injured limb of a second person.

Figure 9B:
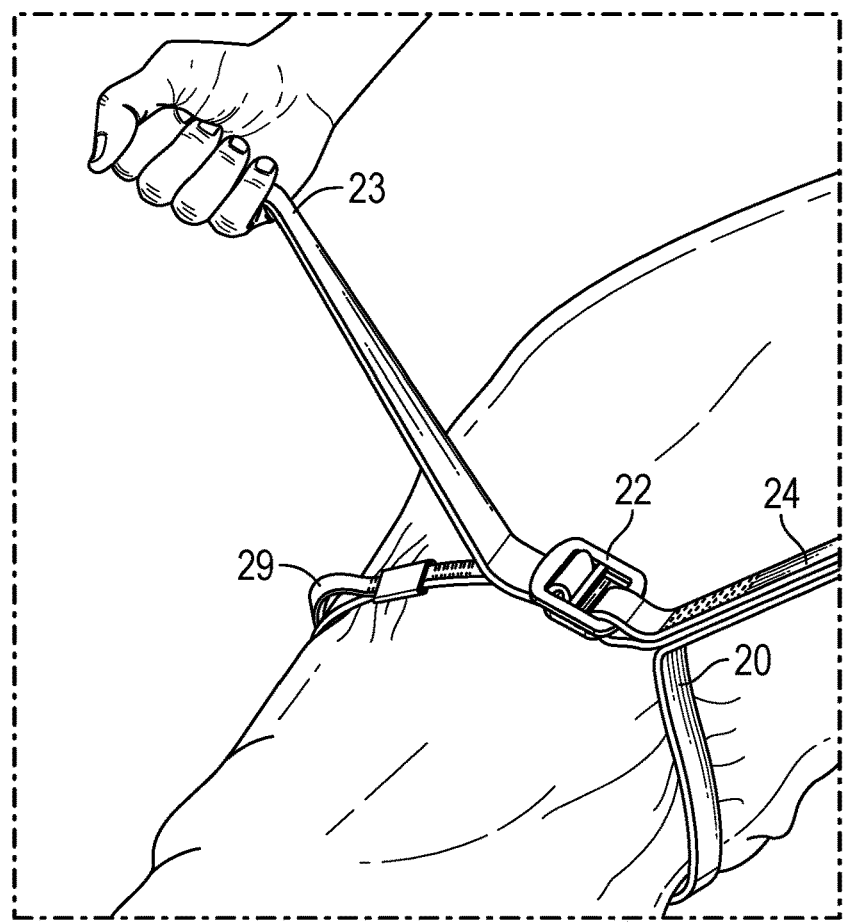
FIG. 9B is a front view of a combined tourniquet and climbing harness system according to the present disclosure, showing a step of positioning and tightening a harness thigh strap for use as a tourniquet upon the limb of a person.

FIG. 9B illustrates the step of positioning the tourniquet thigh strap 20 at the appropriate location on the injured limb. The user can manually grasp the ends 23, 24 of tourniquet strap 20 and adjust its position on the limb, by shifting it up or down the axis of the limb, and/or slidably revolving it around the limb as needed.

Figure 9C:
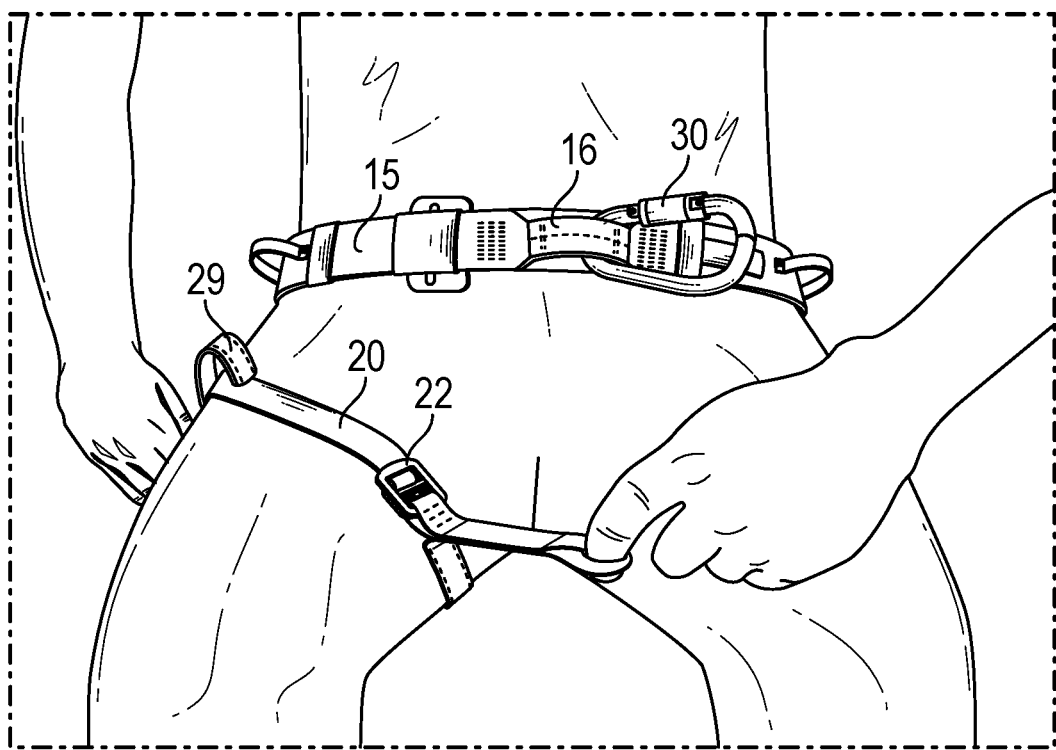
FIG. 9C is a front view of a combined tourniquet and climbing harness system according to the present disclosure, showing a step of positioning the harness thigh strap for use as a tourniquet upon the limb of a person.

Attention is invited to FIGS. 9B and 9C. In a preferred embodiment, the strap buckle 22 is a ladder-type, or similar type, of buckling that permits a controlled deliberate adjustment of the effective length of the looped strap 20 (e.g., by releasing and sliding a length of the strap 20 though the buckle, and then re-securing the buckle). For example, the free end 23 and the second end 24 (having the strap loop 26) may be firmly grasped, and the tourniquet thigh strap 20 is tightened around the limb by means of the adjustment buckle 22. The tourniquet thigh strap 20 accordingly can be preliminarily tightened snugly around the limb by adjusting the effective circumferential length of the looped strap 20.

Figure 9D:
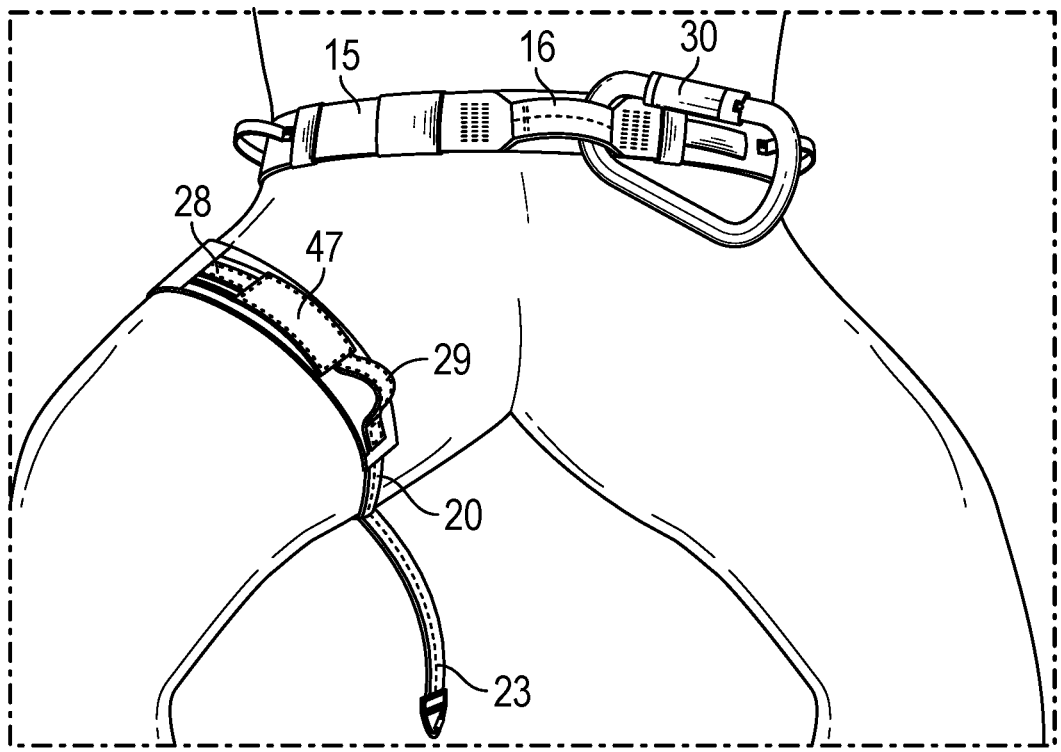
FIG. 9D is a front view of a combined tourniquet and climbing harness system according to the present disclosure, showing a step of locating the harness thigh strap to be well-positioned for use as a tourniquet upon the limb of a person, and showing features of the thigh strap for permitting the strap to function as a tourniquet.

Combined reference is made to FIGS. 9C and 9D. The tourniquet thigh strap 20 preferably is slidably positioned around the affected limb, as may be needed, to bring the carabiner holder loop 28 into optimal location to be accessed (by the user) in the tourniquet procedure. The main carabiner 30 is available for use in the tourniquet procedure; it can be removed from the loop 16 and employed as a windlass for tightening the tourniquet.

Figure 9E:
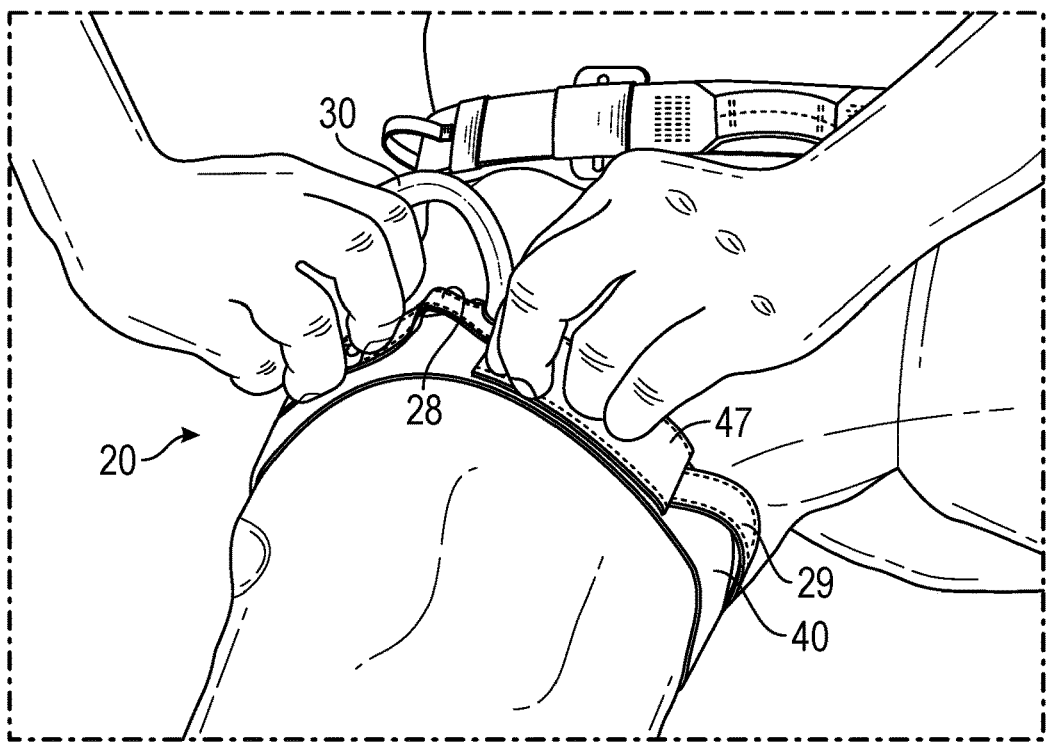
FIG. 9E is a front view of a combined tourniquet and climbing harness system according to the present disclosure, showing a step of engaging a carabiner with a first loop on the tourniquet thigh strap, preparatory to using the thigh strap as a tourniquet.
Figure 9F:
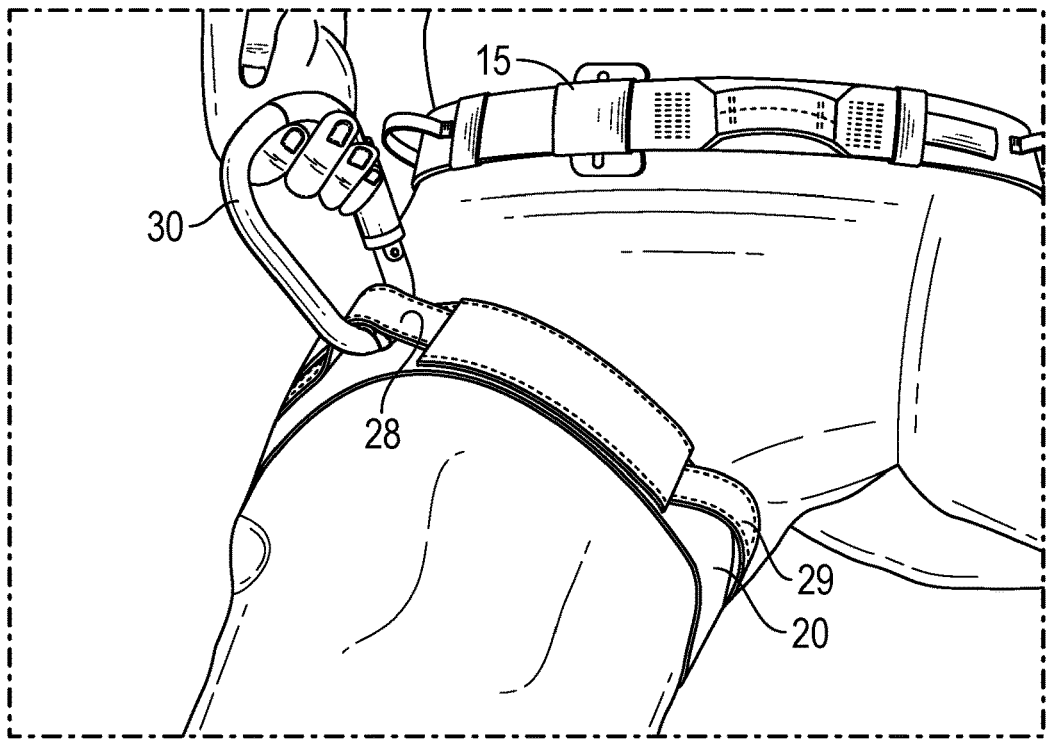
FIG. 9F is a front view, similar to that of FIG. 9E, of a combined tourniquet and climbing harness system according to the present disclosure, showing a step of beginning to use a carabiner as a torsion tool in order to tighten the thigh strap as a tourniquet.

With the holder loop 28 in position for use, the user engages an item with the holder loop by inserting the item between the holder loop 28 and the body 40 of the tourniquet thigh strap 20. The item thus engaged with the holder loop 28 is used as a torsion tool (windlass) for tightening the tourniquet strap. As illustrated in FIGS. 9E and 9F, the windlass item preferably is a carabiner, for instance the main carabiner 30 detached from the belt's carabiner loop 16 and immediately connectably engaged with the carabiner holder loop 28. An advantage of the invention is realized, there necessarily being a carabiner 30 immediately at hand for use as a windlass; a carabiner nearly always is in use in operative conjunction with a climbing harness system. Referring particularly to FIG. 9F, a carabiner serves according to this disclosure as a windlass tool for twisting the carabiner holder loop 28 to execute the constricting function of the tourniquet.

Figure 9G:
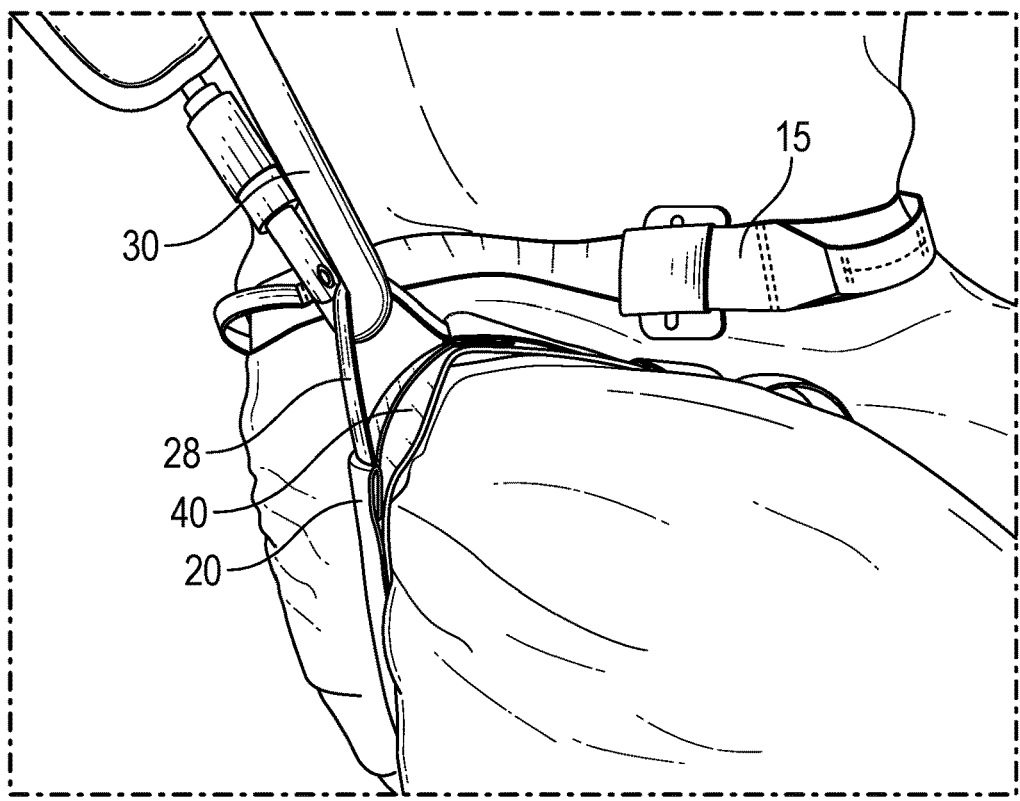
FIGS. 9G and 9H are front views, FIG. 9H being an enlarged view, related to FIG. 9F, of a combined tourniquet and climbing harness system according to the present disclosure, showing a step of using a carabiner as a windlass to twist a first loop (and to continue twisting the first loop until cessation of hemorrhaging) on the tourniquet thigh strap has.
Figure 9H:
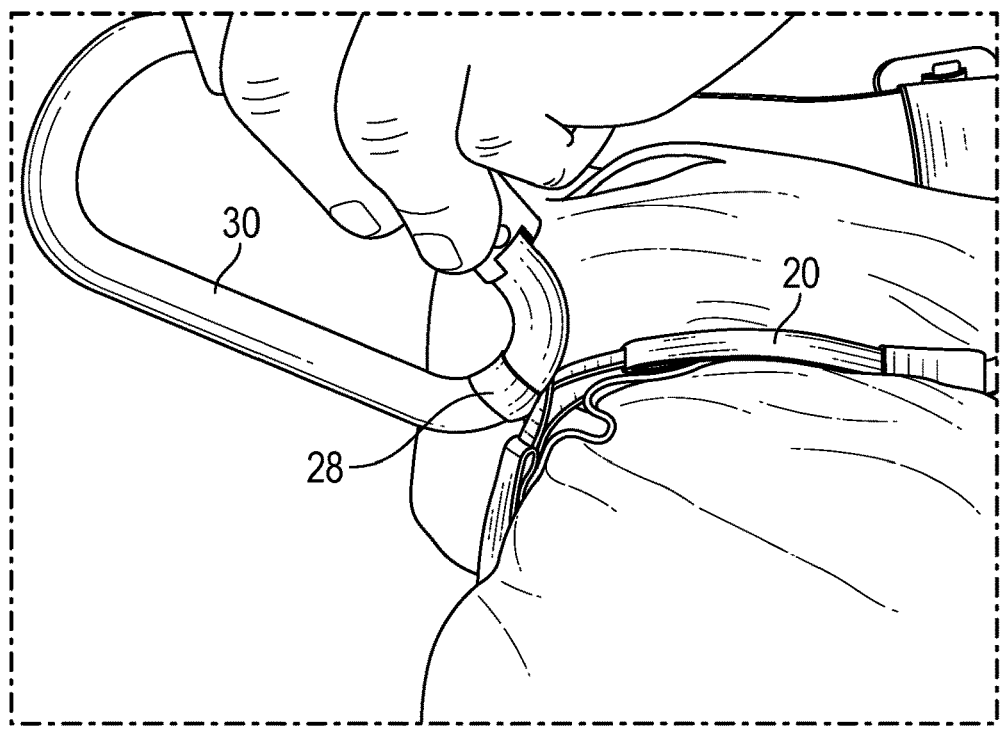

As illustrated by consecutive reference to FIGS. 9G and 9H, the user grasps the torsion tool or windlass carabiner 30 and manually rotates it around an imaginary axis of rotation oriented generally oblique to the body of the tourniquet thigh strap 20. Such rotation shortens the effective length of the strip 44 (between its ends 45, 46) of the carabiner holder loop 28. Consequently, the effective circumferential length of the overall loop of the tourniquet thigh strap 20 likewise is shortened, resulting in the constriction of the patent's limb to reduce the bleeding.

Figure 9I:
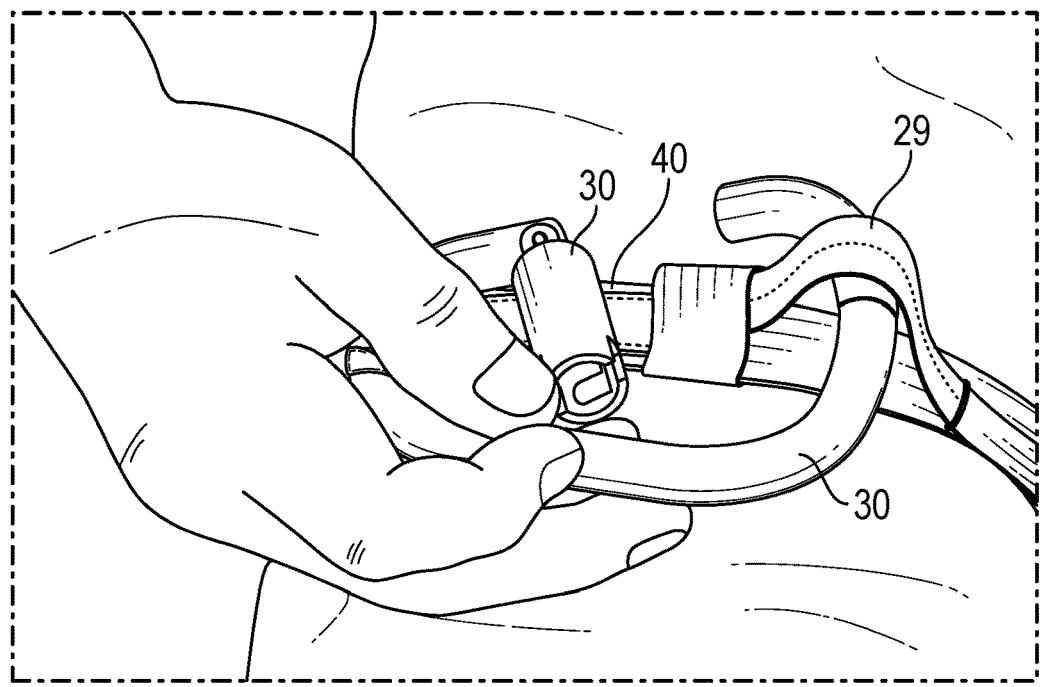
FIG. 9I is an enlarged view of a portion of the tourniquet thigh strap of the system according to the present disclosure, showing the step of beginning to engage the windlass carabiner with a second loop on the thigh strap, thereby to maintain and secure the thigh strap in use as a tourniquet upon the limb of a patient.

The windlass carabiner 30 is then rotated the requisite number of times in the user's judgment to shorten the effective length of the holder loop 28 thereby to constrict the tourniquet thigh strap 20 to restrict blood flow. It is then desirable to have some means to maintain the torsion item/tool, e.g., windlass carabiner 30, in position. The torsion item or windlass carabiner must not be allowed non-deliberately to counter-rotate, which would release the tourniquet's constricted condition. In the system according to the present disclosure, the tourniquet position of the windlass carabiner 30 is maintained by the advantageous engagement of the torsion item with the second loop. Most basically, this engagement my simply be the act of inserting a portion of the torsion item into the second loop. In the preferred embodiment, this engagement of the torsion item with the second loop is the act of clipping of the carabiner to the nearby second loop, e.g., the second, autoblock, loop 29. This step of clipping the carabiner 30 to a second loop 29 is shown in FIG. 9I. Thus clippably engaged with the second loop 29, the windlass carabiner 30 is maintained in its "tightened" position to maintain the constricted condition of the tourniquet thigh strap 20. The user thus is freed from the need to hold manually the carabiner 30 in position for continued tourniquet function.

Figure 9J:
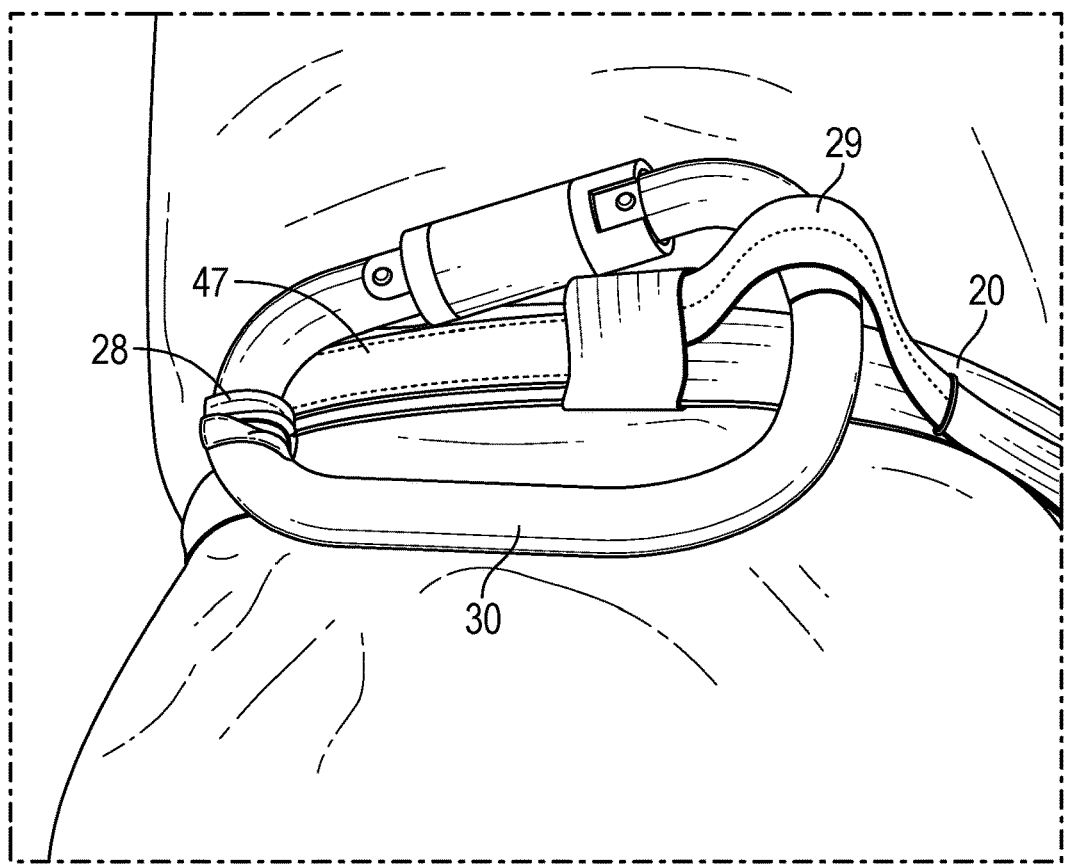
FIG. 9J is an enlarged view, related to the view of FIG. 9I, of a portion of the tourniquet thigh strap of the system according to the present disclosure, showing the step of fully engaging the windlass carabiner with the second loop on the thigh strap, thereby to maintain and secure the thigh strap in use as a tourniquet upon the limb of a patient.

Accordingly, at the conclusion of the tourniquet method according to this disclosure, a carabiner 30 that has been taken from some handy location on the harness belt 15 or thigh strap 20 is held in position for as long as medically indicated to maintain the tourniquet function, as shown in FIG. 9J. The user's hands are freed for use on other urgent tasks further to obtaining medial help for himself or his patient—including evacuation to a first aid station or hospital.

Figure 10A:
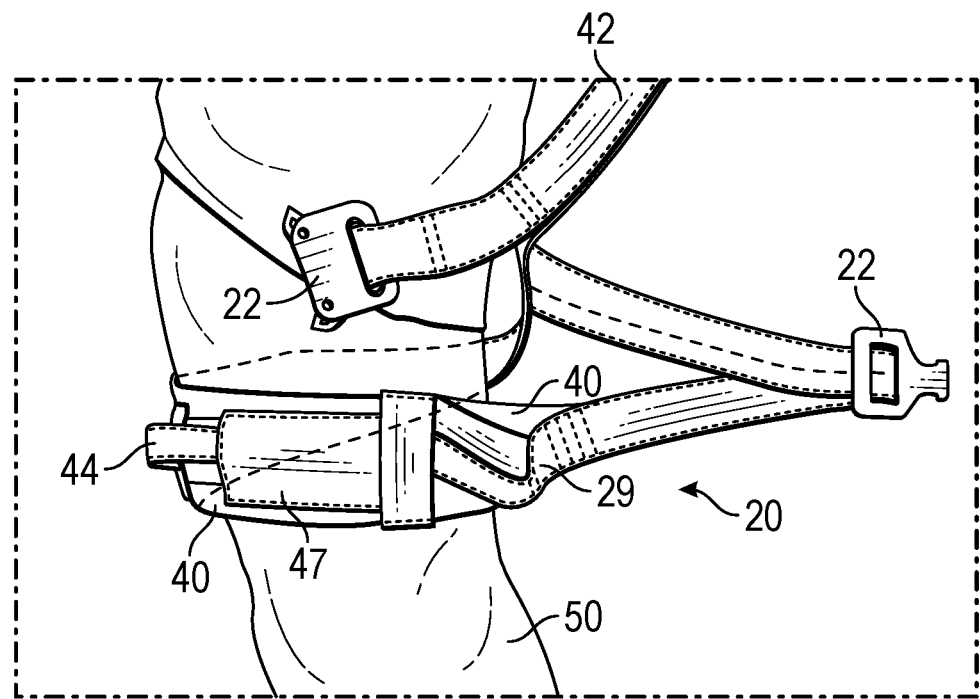
FIGS. 10A-D are a series of views, showing sequentially the steps for using the tourniquet thigh strap of the system according to the present disclosure to apply a tourniquet to an arm.
Figure 10B:
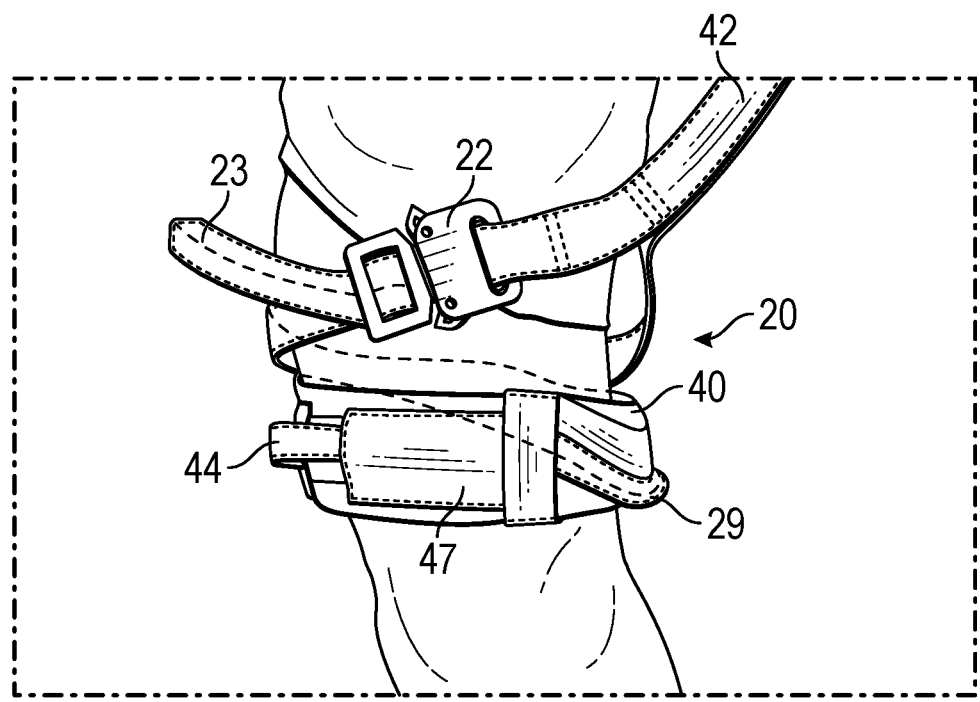
Figure 10C:
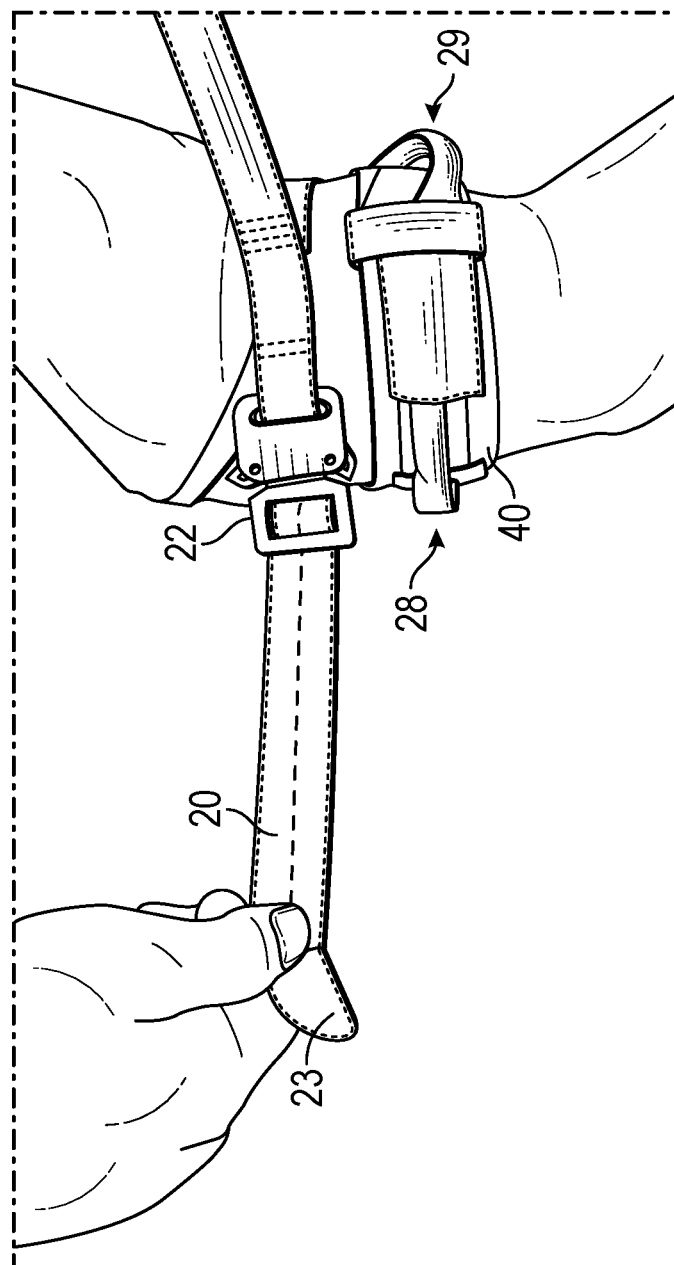
Figure 10D:
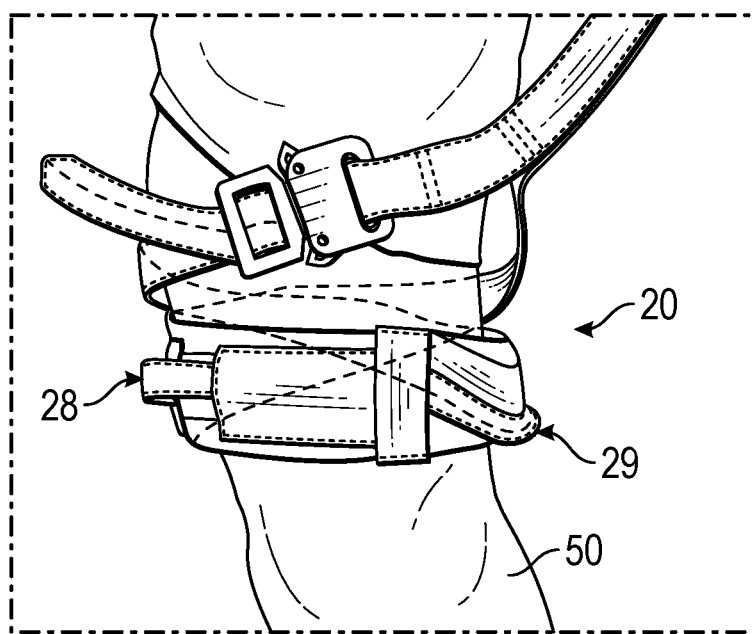

It is readily understood by a person skilled in the art that the system and method according to the present disclosure are suited for use in providing an emergency tourniquet to a patent's injured arm, rather than an injured leg. Serial consideration of FIGS. 10A-D illustrates how the thigh strap can be applied as a tourniquet to an upper or lower arm. FIG. 10A shows that the thigh strap 20 can be wrapped twice (2×360°) around the patient's arm 50; the need to pass the thigh strap 20 around the arm two times may be needed or desired due to the circumferential length of the thigh strap otherwise being too long. As FIG. 10A shows, the thigh strap 20 in this mode of application nevertheless features its useful components as described hereinabove, including the thigh strap main body 40, the buckle 22, the fabric strip 44 defining in part the holder loop 28, the second loop 29, the reinforcing overlay layer 47 which itself is affixed permanently to the body 40, and a segment 42 of the body 40 is doubled back and sewn securely to itself to define the climbing rated strap loop 26 (not shown in FIG. 10A). The strap 20 is wrapped twice around the arm 50, and the buckle 22 engaged to close the double loop, as seen in FIG. 10B. The body 40 of the strap 20 can be shifted and drawn frictionally through a portion of the buckle 22, according to known art, to tighten the double loop as indicated in FIG. 10C. Referring to FIG. 10C, the doubly looped strap 20 is thus arranged to receive a torsion item or tool (not depicted in FIG. 10D), such as a carabiner, through the holder loop 28 to twist the loop to effectuate the tourniquet procedure, as described previously herein. After the carabiner or other torsion item has been rotated to twist the loop 28 to construct the injured arm, an end of the item can be inserted through the second loop 29 to hold the item in the twisted condition. If the torsion item is a carabiner, it can be clipped around the second loop 29 while yet twistably engaged with the holder loop 28. Accordingly, the second loop 29 holds the torsion item in position to maintain the constriction on the injured limb.

A method according to this disclosure accordingly includes several main steps. There is provided a climbing harness system that includes a thigh strap portion and a harness belt portion. Loops on two thigh strap portions are connected, as with a carabiner, to a main carabiner loop on the harness belt portion to provide a sitting harness system. At least one of the thigh straps portions is provided with a holding loop and a second loop, which second loop may be an autoblock loop. The method of the present invention includes the steps of detaching at least one of the thigh straps from the harness belt, to free the thigh strap for use as the loop strap of a tourniquet. The thigh strap is positioned appropriately on the injured limb of a person, and a windlass or torsion item (preferably a carabiner) is used as a torsion tool to constrict the thigh strap on the injured limb. Preferably a windlass carabiner is operatively engaged with the holding loop. The windlass carabiner is rotated to twist the carabiner holding loop, to reduce the effective length of the holding loop, which in turn reduces controllably the effective circumference of the looped thigh strap. The thigh strap thus is tightened around the injured limb (arm and/or leg) to function as a tourniquet. The windlass carabiner is clippably engaged with the second or autoblock loop to maintain the windlass carabiner in its proper position to hold the carabiner holding loop in its twisted condition, thereby also holding the tourniquet thigh strap in its constricted condition to stanch bleeding from the injured limb.

Although the invention has been described in detail with particular reference to these preferred embodiments, other embodiments can achieve the same results. The present inventive method can be practiced by employing generally conventional materials and equipment. Accordingly, the details of such materials and equipment are not set forth herein in detail. In this description, specific details are set forth, such as specific materials, structures, chemicals, processes, etc., in order to provide a thorough understanding of the present invention. However, as one having ordinary skill in the art would recognize, the present invention can be practiced without resorting strictly only to the details specifically set forth. In other instances, well known processing structures have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover in the appended claims all such modifications and equivalents.

I claim:

1. A method for applying a tourniquet to an injured limb, comprising:
   providing a climbing harness system comprising a main belt and a thigh strap having a body;
   disposing on the thigh strap a holder loop and a second loop proximate to the holder loop;
   releasably engaging the thigh strap to the main belt;
   wrapping the main belt about a user's upper hips;
   wrapping the thigh strap around the user's thigh, and releasably engaging the thigh strap to define a closed loop;
   engaging the harness system with a rope, and climbing with the rope;
   disengaging the thigh strap from the main belt;
   looping the thigh strap around the injured limb;
   engaging a torsion item with the holder loop by inserting the item between the holder loop and the body of the thigh strap;
   rotating the torsion item to twist the holder loop, thereby shortening an effective circumferential length of the closed loop of the thigh strap, and constricting the injured limb;
   engaging the torsion item with the second loop to maintain the holder loop in a twisted condition.

2. The method of claim 1 wherein disposing on the thigh strap the holder loop comprises securely attaching to the strap body two ends of a loop strip of flexible fabric.

3. The method of claim 2 wherein securely attaching two ends of the strip comprises:
   affixing a reinforcing overlay layer to the strap body;
   sewing the two ends of the strip between the strap body and the reinforcing overlay layer; and
   defining with the loop strip the holder loop distending a distance from the body.

4. The method of claim 2 further comprising providing the strap body with a bendable stiffener element substantially adjacent the loop strip.

5. The method of claim 1 wherein releasably engaging the thigh strap to the main belt comprises:
   providing a center main loop securely attached on the main belt;
   defining on the thigh strap a main strap loop; and
   disposing a carabiner through the center main loop and through the main strap loop, and closing the carabiner.

6. The method of claim 5 wherein disengaging the thigh strap from the main belt comprises opening the carabiner and detaching it from the center loop and from the main strap loop.

7. The method of claim 6 wherein engaging the torsion item comprises engaging the carabiner.

8. The method of claim 7 wherein rotating the item comprises rotating the carabiner.

9. The method of claim 8 wherein rotating the carabiner comprises rotating the carabiner around an imaginary axis of rotation oriented generally oblique to the strap body.

10. The method of claim 9 wherein engaging the torsion item with the second loop comprises clipping the carabiner to the second loop.

11. The method of claim 1 wherein releasably engaging the thigh strap to define the closed loop comprises:
    attaching a buckle at an intermediate location on the thigh strap; and
    engaging a first free end of the thigh strap with the buckle.

12. The method of claim 11, further comprising tightening the closed loop on the injured limb by moving the thigh strap relative to the buckle.

13. The method of claim 11 wherein defining on the thigh strap a main strap loop comprises folding a second end portion of the thigh strap upon itself, and sewing the strap securely to itself.

14. The method of claim 1 wherein engaging the torsion item comprises engaging a carabiner.

15. The method of claim 14 wherein engaging the torsion item with the second loop comprises clipping the carabiner to the second loop.

16. A method for applying a tourniquet to an injured limb, comprising:
    providing a climbing harness system comprising a main belt and a thigh strap having a body;
    disposing on the thigh strap a holder loop and a second loop proximate to the holder loop;
    releasably engaging the thigh strap to the main belt, comprising:
       providing a center main loop on the main belt;
       defining on the thigh strap a main strap loop; and
       disposing a carabiner through the center main loop and through the main strap loop, and closing the carabiner;
    wrapping the main belt about a user's upper hips;
    wrapping the thigh strap around the user's thigh, and releasably engaging the thigh strap to define a closed loop;
    disengaging the thigh strap from the main belt, comprising opening the carabiner and detaching it from the center loop and from the main strap loop;
    looping the thigh strap around the injured limb;
    engaging the carabiner with the holder loop by inserting the carabiner between the holder loop and the body of the thigh strap;
    rotating the carabiner to twist the holder loop, thereby shortening an effective circumferential length of the closed loop of the thigh strap, and constricting the injured limb; and
    engaging the carabiner with the second loop to maintain the holder loop in a twisted condition.

17. A method for applying a climbing harness as a tourniquet to an injured limb, comprising:
    providing the climbing harness with a main belt and a thigh strap having a body;
    securing on the main belt a center loop means through which a carabiner may be removably attached to the main belt;
    disposing on the thigh strap a holder loop and a second loop proximate to the holder loop;
    wrapping the main belt about a user's upper hips;

releasably engaging together with the carabiner the center loop and the thigh strap;

wrapping the thigh strap around the user's thigh, and releasably engaging the thigh strap to define a closed loop;

engaging the harness system with a rope, and climbing with the rope;

disengaging the thigh strap from the main belt;

looping the thigh strap around the injured limb;

engaging a torsion item with the holder loop by inserting the item between the holder loop and the body of the thigh strap;

rotating the torsion item to twist the holder loop, thereby shortening an effective circumferential length of the closed loop of the thigh strap, and constricting the injured limb;

engaging the torsion item with the second loop to maintain the holder loop in a twisted condition.

18. The method of claim 17 wherein the step of disposing the holder loop comprises securely attaching to the strap body two ends of a strip of flexible fabric.

19. The method of claim 18 wherein:

attaching to the strap body two ends of the strip comprises the step of affixing a reinforcing overlay layer to the strap body; and sewing the two ends of the strip between the strap body and the reinforcing overlay layer, so that the strip defines the holder loop distending a distance from the strap body.

\* \* \* \* \*